United States Patent [19]

Shassere et al.

[11] Patent Number: 5,698,398
[45] Date of Patent: Dec. 16, 1997

[54] CONTROL COMPOSITIONS FOR DETERMINATION OF MOLECULAR CYTOGENETIC ABNORMALITIES WITH DNA PROBES

[76] Inventors: Christine J. Shassere, 1613 Preston Rd.; Steven A. Seelig, 2409 Remington Dr., both of Naperville, Ill. 60565

[21] Appl. No.: 538,768

[22] Filed: Oct. 5, 1995

Related U.S. Application Data

[63] Continuation of Ser. No. 139,351, Oct. 18, 1993, abandoned.
[51] Int. Cl.[6] ..................................................... C12Q 1/68
[52] U.S. Cl. ........................ 435/6; 435/240.2; 435/240.25
[58] Field of Search ........................ 435/6, 240.2, 240.3, 435/810, 240.25

[56] References Cited

U.S. PATENT DOCUMENTS

5,059,518 10/1991 Kortright et al. ............................ 435/6
5,409,826 4/1995 Maples et al. ........................ 435/240.2

OTHER PUBLICATIONS van Dekken et al., *Cancer* 66, 491–497 (1990).

Klinger et al., *Am. J. Hum. Genet.* 51, 55–65 (1992–Jul.).

Paxton et al., *Int. Soc. Analy. Cytol.*, 16 (Mar. 1993).

*Primary Examiner*—Kenneth R. Horlick

[57] ABSTRACT

Quality control compositions suitable as sample specimens to measure performance of DNA probe tests which determine cytogenetic abnormalities, such as chromosome copy number, of cells in a tissue sample are disclosed. The control compositions comprise a suspension of fixed cells having an artificial concentration of cells exhibiting chromosome specific aneuploidy in one or more specific chromosomes.

27 Claims, No Drawings

CONTROL COMPOSITIONS FOR DETERMINATION OF MOLECULAR CYTOGENETIC ABNORMALITIES WITH DNA PROBES

This is a continuation of application Ser. No. 08/139,351, filed Oct. 18, 1993, abandoned.

FIELD OF THE INVENTION

This invention relates generally to quality control standards for use with in-situ hybridization procedures using DNA probes, and more particularly to control compositions comprising an artificial concentration of cells exhibiting at least one molecular cytogenetic abnormality, which are useful as quality control standards for DNA probes.

BACKGROUND

Molecular cytogenetics is the evaluation and determination on a molecular level of an organism's genetic material, such as the DNA contained in human chromosomes. Molecular cytogenetics is of growing research and clinical significance because of the recognition that cancer and other diseases result from changes in the DNA of a chromosome or from the inherited DNA make-up of a chromosome. Molecular cytogenetics involves attempts to establish correlations between specific diseases and genetic events, such as the existence of an abnormal number of a particular chromosome, a condition called aneuploidy. For example, acute myelogenous leukemia has been correlated to the presence in the affected blood cells of three copies, compared to the normal two copies, of chromosome 8, a condition called "trisomy 8". Therefore, molecular cytogenetic analysis, such as methods for chromosome enumeration, is of diagnostic and prognostic significance to the physician.

Fluorescence In Situ Hybridization ("FISH") is a molecular cytogenetic technique of increasing use. FISH involves the use of DNA probes to determine if a particular nucleotide sequence is present in the chromosomal DNA of particular cells. These DNA probes comprise a nucleotide sequence complementary to a specific target DNA nucleotide sequence in a chromosome, wherein the probe is directly labeled with a fluorescent molecule or indirectly labelled with an antibody which can be bound to a fluorescing material. In use, the DNA probe is mixed with the cell sample under conditions which permit hybridization of the nucleotide sequence of the DNA probe to its corresponding target nucleotide sequence in the chromosome, if present, to form a hybrid reaction complex. If formed, the hybrid reaction complex is subsequently detected with a fluorescent microscope. An example of commercially available DNA probes for FISH use is the SpectrumCEP™ Chromosome Enumeration Probes available from Imagenetics (Framingham, Mass.). These chromosome enumeration probes each comprise direct fluorescently labelled DNA probes containing satellite DNA sequences (alpha, beta satellite III) which are commonly complementary to the centromere region of a particular chromosome. In addition to being complementary to the centromere, these satellite DNA sequences may be complementary to other parts of the particular chromosome. These chromosome enumeration probes thus permit accurate determination of chromosome specific aneuploidy (chromosomal copy number) in the cells of a particular tissue sample.

One problem for the use of FISH to determine chromosomal copy number is the absence of any commercially available control standards to verify correct analysis. The U.S. Clinical Laboratories Improvement Act of 1990 also mandates that clinical testing laboratories perform certain quality control analysis in relation to tests performed by the clinical laboratories. With regard to control standards for chromosomal copy number determination, the only presently available control technique is to have on hand appropriate cell lines of known chromosomal aneuploidy which can be used to calibrate the technique and analysis used. This is not practical for the majority of clinical laboratories which will not have access to appropriate cell lines. There is therefore a need for control test standards having "artificial" concentrations of aneuploid cells which can be used to calibrate chromosome enumeration analysis.

Applicants are not aware of any literature reference describing the use of test standards having artificial concentrations of aneuploidy cells for use in calibration of chromosome enumeration techniques. A cell mixture for use in FISH research is disclosed in "Detection of Male Cells in Mixtures Containing Varying Proportions of Male and Female Cells by Fluorescence In Situ Hybridization and G-Banding", A. White et al., CYTOMETRY, Vol. 14, pp. 9–15, 1993. The disclosed cell mixtures contained normal cells and were used to assess the ability of FISH to detect male cells. These mixtures did not comprise cells containing a molecular cytogenetic abnormality.

"Use of Aneuploid Cell Lines as Standards and Calibrators in DNA Analysis", H. Paxton, et al., International Society for Analytic Cytology: 1993 Abstracts, page 16, published March 1993, describes "standard preparations" which contain tumor cells mixed with human peripheral blood lymphocytes ("PBL's"). These preparations are not disclosed for use with molecular cytogenetic determination of a chromosome specific abnormality, such as chromosome specific aneuploidy. The described standard preparations were used in evaluation by flow cytometry for the percentage of aneuploid recovery, aneuploid peaks and reproducibility of assay value. Flow cytometry is only capable of gross chromosomal aneuploidy measurement; it does not determine whether specific chromosomes are aneuploid. Furthermore, the standard preparations disclosed therein are cells with grossly different morphologies. The different morphologies make the disclosed preparations unsuitable in chromosomal copy number determination because of possible observer bias in the results. Chromosomal copy number determination involves visual examination; cells with grossly different morphology can lead to inaccurate analysis. Finally, the Abstract does not disclose the method of manufacture nor does it disclose control compositions comprising tumor cells from two or more sources.

Therefore, control compositions useful in conjunction with determinations of specific molecular cytogenetic abnormalities on a specific chromosome, such as chromosomal copy number determinations with DNA probes, are not available nor disclosed. It is an object of the invention to provide control compositions having an "artificial" concentration of cells with chromosome specific abnormalities suitable to measure performance of molecular cytogenetic techniques. It is a further object to provide methods for manufacture of such control compositions. Another object is to provide control compostions for performance measurement of chromosome enumeration DNA probes. Other objects will appear below.

SUMMARY OF THE INVENTION

The invention broadly comprises control compositions suitable to measure performance of tests which determine specific molecular cytogenetic abnormalities on specific chromosomes of individual cells, comprising a suspension media and a fixed cell mixture which comprises: (i) cells from at least two sources having similar morphology, (ii) a total cell concentration above about 10,000 cells per milliliter of control composition and (iii) a predetermined, "artificial" concentration of abnormality-containing cells exhibiting at least one molecular cytogenetic abnormality in at least one chromosome. The inventive compositions are used as sample specimens and provide clinical and research laboratories using techniques to measure cytogenetic abnormalities, such as FISH performed with chromosome enumeration DNA probes, with the ability to verify proper performance of their analytic techniques. The control compositions can comprise cells with chromosome specific aneuploidy for each human chromosome and therefore serve as controls for a wide number of chromosome enumeration tests. Preferably, the control compositions comprise fixed human cells having an artificial concentration of cells exhibiting aneuploidy in at least one of chromosomes 1 through 22, X and Y. The inventive compositions can further comprise two or more different types of abnormality-containing cells, each type exhibiting a different chromosome specific abnormality, thereby being suitable as a simultaneous control for more than one DNA probe.

The invention further comprises a method for the manufacture of the inventive compositions. Applicants' early attempts to manufacture the inventive compositions involved determination of the cell count for each of two different cell sources, one having a high percentage exhibiting aneuploidy in a desired chromosome cell (the "abnormal" source) and the other having a low percentage of cells exhibiting aneuploidy in a desired chromosome (the "normal" source), each source comprising cells in suspension in a fixative solution. However, addition of the fixative solution to each source prior to mixing of the two cell sources resulted in suspensions for which Applicants were unable to determine cell concentration. Applicants found, instead, that the inventive compositions could be made by a method comprising: mixing a first cell solution with a second cell solution, each of said cell solutions having a known cell concentration and comprising a media capable of sustaining cell multiplication, in a desired ratio to produce an intermediate mixed cell suspension; treating the intermediate suspension to produce a control composition comprising fixed cells; and determining the chromosome specific abnormality content of cells in the control composition.

The method of the invention can be used to produce a predetermined, "artificial" concentration of cells exhibiting specific molecular cytogenetic abnormality content in one or more chromosomes, by selection of the appropriate first and second cell sources and by mixing of the cell sources in the desired ratios. The inventive method has the further advantage of reliable reproduction of the inventive compositions.

DETAILED DESCRIPTION OF THE INVENTION

The compositions of the invention comprise an artificial concentration of cells exhibiting at least one molecular cytogenetic abnormality in at least one chromosome. The control compositions comprise an "artificial" concentration of cells exhibiting the cytogenetic abnormality, which is preferably chromosome specific aneuploidy. By artificial concentration, Applicants mean that the control composition has a preselected concentration of cells, based on total cell content of the composition, which exhibits the specific cytogenetic abnormality in the specified chromosome. The control compositions can also comprise cells exhibiting: molecular cytogenetic abnormalities in more than one chromosome, more than one molecular cytogenetic abnormality in the same chromosome, or any combination thereof. The types of cytogenetic abnormalities include DNA sequence translocations between chromosomes, DNA sequence deletions from a chromosome, DNA sequence amplification on a chromosome, and chromosomal aneuploidy. As is known in the art of molecular cytogenetics, even normal cell populations contain low ("background") percentages of cells which contain cytogenetic abnormalities. The background level varies with the specific abnormality, but is believed generally less than 2.0% of total cells in the population. Thus, in the control compositions of the invention, the artificial concentration of cells with an abnormality is any preselected percentage, based on total cells in the control composition, which is greater than the background level of normal cells exhibiting the abnormality. The control compositions comprise cells from at least two cell sources, one of low ("normal") content of cells exhibiting the specific cytogenetic abnormality, the other of higher ("abnormal") content of cells exhibiting the specific abnormality.

The inventive compositions preferably comprise control standards useful to measure the performance of chromosome enumeration DNA probes, such as the SpectrumCEP™ probes from Imagenetics (Framingham, Mass.). The control compositions of the invention comprise cells derived from a minimum of two sources, one cell source having a "normal" aneuploidy content and the second having an "abnormal" aneuploidy content. Human cells are normally diploid, i.e. they each contain two copies of chromosomes 1–22 and one pair of sex chromosomes, X and Y. Any number of chromosomes other than two of each chromosome per cell is termed aneuploid. However, even healthy, normal human cells contain a low background percentage of cells exhibiting aneuploidy in one or more chromosomes. As used herein, normal aneuploidy content means that the cells exhibit only a low background concentration of cells exhibiting chromosome specific aneuploidy in one or more chromosomes. The background level is preferably less than about 2.0% of total cells exhibiting aneuploidy in the desired chromosome. The second cell source contains a significant percentage of cells exhibiting chromosome specific aneuploidy in the desired chromosome or chromosomes. Thus, the abnormal aneuploidy content is the desired percentage of cells exhibiting the specific chromosome anueploidy. Further, the second cell source can have individual cells exhibiting aneuploidy in more than one chromosome. The use of two or more cell sources to produce the inventive compositions permits adjustment of the abnormality-containing cell content of the control composition to any desired level for any desired chromosome based on cell source selection and on the mixing ratios of the two or more cell sources.

Each of the "normal" and "abnormal" cell sources is from cell lines or cell sources having similar cell morphology, i.e. size, shape and configuration. The reason for this is that the control compositions are primarily used in conjunction with FISH DNA probes which are analyzed with the aid of a fluorescent microscope; the cells in the control should not have widely different cell morphology, so as to avoid introducing observer bias. The similarity of cell morphology for the cell sources is visually assessed. When the compositions comprise more than two cell sources, the likelihood of observer bias can be reduced by having at least two of the cell sources having similar morphology.

The cell sources can be of any source which comprises cells sustainable in vitro by in vitro culture techniques. The cell sources can comprise human bone marrow cells, lymphoid or myeloid, ascitic cells from intraabdominal fluid, cells from pleural effusions, fibroblasts, and cells from solid tumors, preferably primary solid tumors. Preferably the cell sources comprise bone marrow cells, ascitic cells or cells from pleural effusions, because these cells are easier to culture.

Any suitable cell line or cell source can be used for either the first or second cell sources. Preferably, the cell sources are human cell lines, with the source from a tumor cell line having an abnormal aneuploidy content. For example, a cell line with a high concentration of cells exhibiting trisomy 8 can be used to produce a control composition having an artificial concentration of trisomy 8 cells. Such a cell line is the K-562 tumor cell line available as ATCC Deposit No. CCL-243 from the American Tissue Culture Collection (Rockville, Md.). A cell source having a normal background level of aneuploidy in chromosome 8 is the cell line GM06912A, obtained from the NIGMS Human Genetic Mutant Cell Repository (Camden, N.J.). More preferably, each of the first and second cell sources comprise human tumor cells of differing chromosome specific aneuploidy, so that the resulting control compositions are controls for more than one type of chromosome specific aneuploidy tests. The inventive compositions can also comprise cells from more than two sources, for example, a cell source of normal aneuploidy content in each of two chromosomes, and two other cell sources, each of abnormal anueploidy content in one of the two chromosomes.

Applicants do not believe it necessary to perform a preliminary cell sorting of the cell sources to ensure that substantially all cells in each cell source are at substantially the same stage in their cell cycles. However, it is within the scope of the invention to use cell sources which comprise cells which are substantially within the same cell cycle stage to produce the inventive compositions. The necessary cell sorting to produce such cell sources can be performed by flow cytometry.

Any suitable artificial concentration of the abnormality-containing cell content can be used and preferably will comprise 5 to 95 percent abnormality-containing cells, based on total cells in the composition. This range is preferred because a preferred control composition is one comprising cells from one source with a 95% concentration of cells exhibiting a first abnormality and a second source with cells exhibiting 95% concentration of cells with a second abnormality. Preferably the artificial concentration is one of three concentrations: about 5% total cell content, about 10% total cell content and about 50% of total cell content. Thus the inventive compositions comprise artificial concentrations of cells exhibiting a specific molecular cytogenetic abnormality in a particular chromosome in the range of about 4 to about 6 percent of total cell content, about 8 to about 12 percent of total cell content, and about 48 to about 52 percent of total cell content. Other abnormal artificial cell concentrations are possible, if desired. Further, the control compositions can comprise cells exhibiting an artificial concentration of aneuploid cells for one chromosome, and a second artificial concentration of cells exhibiting aneuploidy in a separate chromosome or chromosomes.

The control compositions are prepared using sufficient suspension media to produce a minimum cell concentration which, when the composition is used to prepare a glass microscope hybridization slide, results in a cell count of 500 cells per slide. Preferably the cell concentration in the control composition is sufficient to produce a slide count of at least 1,000 cells per slide. These mounts are believed to be of above about 10,000 cells per milliliter of control composition (for 500 cells/hybridization slide) and above about 20,000 cells per milliliter of control composition (for 1000 cells/hybridization slide). This minimum amount is preferred because of the intended use of the compositions: cell concentrations below this amount can lead to inaccurate hybridization analysis resulting from too few cells on the hybridization slide.

The inventive compositions are used as control standards in the measurement of the performance of techniques for determination of molecular cytogenetic abnormalities like chromosomal copy number. The control compositions are particularly suitable as control standards for use with chromosome enumeration DNA probes for FISH which determine chromosome copy number of cells in a particular specimen tissue sample. The control compositions comprise cell suspensions which are handled similarly to tissue samples undergoing analysis in a clinical or research laboratory. FISH tests employing chromosome enumeration DNA probes involve the preparation of hybridization slides containing the tissue sample to be tested, to which is applied the chromosome enumeration DNA probe under conditions which permit hybridization between the DNA of the tissue sample with the DNA probe. After the hybridization reaction has occurred, the slide is then washed to remove any unreacted probe, and is then analyzed to determine the presence of the hybrid reaction complex comprising the probe and its target nucleotide sequence. Typically the analysis for the presence of the hybrid reaction complex is with the aid of a fluorescent microscope. Similarly, the inventive compositions are used as specimen samples to produce hybridization slides in which chromosomes in the cells in the inventive composition serve as the target for the chromosome enumeration DNA probe. The slides produced from the inventive composition are then tested with the chromosome enumeration probe using any suitable hybridization technique, which for quality control purposes is preferably the identical technique to that used by a laboratory for testing unknown tissue samples. Because the control compositions can be reproduced from a wide variety of cell sources, they can be used as a quality control for use of a wide variety of DNA probes. Use of the control compositions permits the laboratory to assess variables in its use of DNA probes. For example, assessment of temperature affect on hybridization can readily be made.

The invention also comprises a method of manufacture of control compositions for perfomance measurement of chromosome enumeration DNA probes. The manufacturing of the inventive composition begins by obtaining cells from appropriate sources for use as the first and as the second cell source. Each of the cell sources is then counted by any suitable method, such as with a hemocytomer or, preferably, a Coulter counter, to determine cell count of the particular cell source. This data is needed to calculate the appropriate ratio of amounts of the first cell source and amounts of the second cell source to be combined. The percent cells exhibiting the selected chromosomal abnormality, i.e. aneuploidy, in each of the first and second cell sources is then determined. Preferably the first cell source exhibits only a low background level of aneuploidy in the chromosome of interest. The low background level is typically less than 2 percent. Once the cell counts and aneuploidy content of the cell sources are known, they can be mixed in a desired ratio to produce the desired control compositions.

As seen in Comparative Example 1, Applicants determined that mixing of first and second cell sources which had been individually treated with a fixative solution before their combination, was not feasible, because the cell count of the individual cell sources could not be determined due to excessive cell clustering. Therefore, the inventive compositions are produced by addition of a fixative solution, to be used as the suspension media for the inventive compositions, only after the first and second cell sources have been mixed in the desired ratios.

Typically, sources of human cells are available in a media which permits cell multiplication. Applicants prefer to obtain cells in a known growth media comprising electrolytes such as NaCl, KCl, phosphates and a pH buffer salt, for example, minimum essential media (MEM) available from GIBCO/BRL, for use to produce the inventive compositions. The appropriate volume of the cell source is mixed in MEM to produce the first and second cell sources. At the time of determination of the cell count of the cell sources, the growth media does not comprise serum or other additives which aid cell multiplication.

After determining the cell counts and the molecular cytogenetic abnormality content, the first and second cell sources are mixed in a desired ratio to produce an intermediate cell suspension. The intermediate cell suspension is then treated under suitable conditions, for example by centrifuging, to remove the existing growth media in the intermediate cell suspension. After removal of the growth media, the cell pellets are each treated with a hypotonic solution to cause cell swelling. A suitable hyoptonic solution is aqueous KCl solution. After treatment, the hypotonic solution is removed by centrifuging and removal of the supernatent. The resulting cells are then dissolved into a fixative media such as Carnoy's fixative to produce the cell suspension of the invention.

Any suitable fixative solution can be used as the suspension media of the inventive compositions. It is preferred to use a blend of 3/1 by volume methanol and acetic acid because this fixative solution is readily available as Carnoy's fixative and works well.

Any suitable mixing procedure can be used to produced a homogeneous mixture of the cells in the fixative solution. The mixing solution should not be so disruptive as to unduly disturb the cell nuclei. After the cell suspension has been produced, the percent chromosome specific aneuploidy content or other abnormality of this control composition is determined, preferrably by use of a chromosome enumeration probe such as the SpectrumCEP™ chromosome enumeration probe available from Imagenetics, Inc.

In another embodiment the method of the invention further comprises production of hybridization slides comprising the control compositions of the invention. Any suitable slide preparation procedure can be used. Preferrably the control composition is dropped onto a microscope examination slide and stored under nitrogen at −20° C. to await use. The actual amount of control composition added to the hybridization slide is any desired amount and is typically 100 microliters or about 1 drop from a a two milliliter Pasteur pipette.

In another embodiment, the invention comprises a container comprising the control compositions. When packaged in appropriate containers, the control compositions can be transported to customer clinical and research laboratories for use and storage. Any suitable container or package for storing of the cell suspension comprising the fixed cells and suspension media of the invention can be used. Preferrably the containers in this embodiment of the invention comprise a nonreactive, opaque, plastic container of suitable size and having air tight seals. The containers comprising the control compositions can be included in kits, for example, containing more than one type of control composition or containing DNA probes.

The following Examples are illustrative, but not limiting, of the invention.

EXAMPLE 1

A sample of the continuous cell line K-562 was obtained from the American Tissue Culture Collection, Deposit ATCC CCL-243. The K-562 cell line was established from the cells of a fifty-three year old human female with chronic myelogenous leukemia in terminal blast crises. The K-562 cell line has previously been described as exhibiting a high concentration of cells aneuploid in chromosome 8.

A second cell line, GM06912A, was obtained from the NIGMS Human Genetic Mutant Cell Repository in Camden, New Jersey, Depository Number GM06912A. The GM06912A cell line was established from a seventeen year old male, is not known to exhibit any significant aneuploidy in chromosome 8, and has been characterized as exhibiting fragile X syndrome.

The K-562 cell line was used as a starting material to produce the first cell source of the invention and the GM06912A cell line was used as the starting material for the second cell source. Each of these cell lines were separately treated as follows: initially the cell count of each of the cell sources was determined. A 10 milliliter culture of each of the cell lines in standard growth media, MEM, minimum essential media from Gibco/BRL, was treated with 0.2 milliliters of colcemid to arrest cell growth. The mixtures were then allowed to sit for fifteen minutes. Each treated cell source was then centrifuged for ten minutes and aspirated to remove remaining media. The resulting cell pellets from each cell line were then resuspended in a total of about twenty to 30 ml of MEM to total volume of approximately thirty milliliters. Cell counts of the resulting solutions were determined on a hemocytometer after dilution of the cell mixtures with phosphate buffered saline ("PBS") and trypan blue. Sufficient PBS and trypan blue was added to produce a count of approximately 30 to 100 cells per quadrant of the hemacytometer. The cells were then counted in four quadrants in each of the two chambers of the hemacytometer and recorded. The actual number of cells determined was then multiplied by the dilution factor, i.e. the amount of PBS and trypan blue added.

The cell count for the K-562 was determined to be $6.4 \times 10^5$ cells per cc. The cell count for the GM06912A was determined to be $1.17 \times 10^6$ cells per cc. The GM06912A cell suspension was then diluted with MEM to a calculated cell count the same as that for the K-562 cell suspension:

$$9cc\ (1.17 \times 10^6/cc) + 7.5cc\ MEM =$$
$$1.053 \times 10^7\ cells/16.5cc =$$
$$6.4 \times 10^5\ cells\ per\ cc$$

Both the first and second cell sources thus had equivalent cell concentrations. The two cell sources were then mixed to produce three cell suspensions: (1) having about 5% of the cells exhibiting the trisomy 8 of the K-562 cell line, (2) 10% exhibiting trisomy 8; and (3) about 40% exhibiting trisomy 8. The mixtures in Example 1-2, 1-3 and 1-4 were produced by mixing by volume, respectively, 1 part of the K-562 suspension with 1 part of the GM06912A suspension, 1 part of K-562 with 9 parts of GM06912A and 1 part K-562 with 18 parts GMO6192A. Table 1 shows the resulting cell mixtures and controls.

TABLE 1

| EXAMPLE NUMBER | PERCENT TRISOMY 8* | PERCENT GMO6912A* |
|---|---|---|
| 1-1 | 100 | 0 |
| 1-2 | 40 | 95 |
| 1-3 | 10 | 90 |
| 1-4 | 5 | 50 |
| 1-5 | 0 | 100 |

*Based on total cells

After the cell counts were determined and the resulting cell mixtures produced, the mixtures were then immediately harvested by addition of 0.1 ml of colcemid for each approximately 5 ml by volume of the cell mixture or control and allowed to stand for one hour. The mixtures and controls were then incubated for 1 hour at 37° C. in 5% $CO_2/H_2O$ solution. The thus treated cell mixtures and controls were then centrifuged for 10 minutes and any remaining supernatent was also removed. The cell mixtures and controls were then resuspended by the addition of 10 ml of 0.075M KCL and were incubated at 37° in a water bath for 20 minutes. The cell mixtures and controls were then centrifuged again for 10 minutes and the supernatent removed. Two ml of Carnoy's fixative (3/1 by volume methanol/acidic acid) was slowly added and mixed. An additional 6 ml of Carnoy's fixative was added and mixed to produce the fixed cell mixtures and controls. The fixed cell mixtures and fixed cell controls were then allowed to stand for 5 minutes at room temperature and then centrifuged for 10 minutes. The supernatent was removed and the cells were resuspended by the addition of 8.5 ml of Carnoy's fixative to each. The mixtures and controls were again centrifuged for 10 minutes, the supernatent was removed and sufficient additional Carnoy's fixative was added to resuspend the pellet so that the resulting solutions were slightly cloudy.

Hybridization slides (two slides per Example) were then prepared from each of the Examples 1-1 through 1-5 as follows:

Glass microscope slides were dipped in 70% by volume ethanol/$H_2O$ and wiped dry with a wipe. Each slide was dipped briefly into a 3:1 by volume ethanol:acetic acid solution. One to two drops of fixed cell suspension was then immediately dropped onto the microscope slide using a pasteur pipette. The slide was placed in a humidified environment of approximately 50% humidity and approximately 70°–80° C. The slide remained in the humidified environment until the cell and fixative suspension dries on the slide. Slide was removed from the humidified environment and then placed at room temperature/environment for approximately 24 hours before use.

FISH was then performed on each of the slides to determine percent aneuploid cell content as follows:

Slides were placed into a denaturing solution of pH 7.5 comprising 70% formamide and 30% 20 X aqueous sodium chloride/sodium citrate solution ("SSC"), which is 2.99M NaCl and 0.3M Sodium citrate, and maintained at a temperature of 74° C. for 5 minutes. Excess fluid was drained from the slide after removal from the bath. Simultaneously with the slide denaturation, a hybridization mixture comprising 7 microliters of SpectrumCEP Hybridization Buffer, lot no. 9411, obtained from Imagenetics, Framingham, Mass., 1 microliter of SpectrumCEP 8 Orange Chromosome Enumeration Probe, lot number 9431, obtained from Imagenetics, Framingham, Mass., and 2 microliters of $H_2O$ was mixed briefly in a microcentrifuge. The hybridization mixture was then denatured in a 74° C. water bath for 5 minutes. The hybridization mixture was then cooled on an ice bath for 1–5 minutes. The hybridization mixture was then microcentrifuged briefly for approximately 2 seconds and was pipetted 3–5 times each before addition to the slides.

Immediately after removing the slides from the denaturing bath, the slides were placed into 70% ethanol/water wash for 1 minute, removed, touched to the side of a coplin jar maintained at 74° C., placed into an 85% ethanol/water wash for 1 minute, touched to the side of the jar and then placed into a 100% ethanol wash for 1–5 minutes. The slides were then dried, and excess ethanol was drained by blotting the edge of the slide until all visible moisture was gone. The denatured slides were then placed on a 45° C. to 50° C. slide warmer. The slides were maintained on the warmer for at least 3 minutes before application of the hybridization mixture.

To each of the slides, 10 microliters of the hybridization mixture was applied by pipetting directly onto the target. A cover slip was then placed over the hybridization mixture, avoiding formation of bubbles under the cover slip. Rubber cement solution was applied around all edges of the cover slip. The slides were then incubated in an air incubator at 42° C. overnight by placement in an air tight box containing a piece of blotting paper wetted with 3–5 drops of water.

Wash solutions for the post hybridization treatment of the slides were all maintained at 47° C. The slides were removed from the incubator and cover slips removed and placed in a first water bath containing a wash solution of 50% 2 X SSC (0.3M NaCl and 0.03M sodium citrate) and 50% formamide. The slides were agitated gently and allowed to stand in the wash solution for 10 minutes. The slides were removed from the first wash and drained but not dried. The slides were then placed in a second wash solution of the same make-up as the first wash solution for 10 minutes. Again the slides were drained without allowing then to dry and transferred to a third wash solution of the same make-up for 10 minutes. The slides were again drained without allowing to dry. The slides were then transferred to a fourth wash solution comprising 2 X SSC and allowed to stand for 10 minutes. The slides were again drained without allowing to dry and transferred to a fifth wash solution which comprised 2 X SSC and 0.1% detergent NP-40. The slides were allowed to stand in the fifth wash solution for 5 minutes. The slides were then removed, drained thoroughly and allowed to air dry in dim light. Ten microliters of standard counterstain solution comprising 2',6-diamino-phenylindole (DAPI) and p-phenylene diamine and glycerol were then applied to the target area of the slide, and cover slips were placed on the target areas. The slides were then left at room temperature until the hybridization results observed.

Hybridization results were counted by an individual who was blinded to, i.e. not involved in, the experimental preparation, counting 500 cell nuclei per slide using a fluorescence microscope having a dual bandpass DAPI/Spectrum Orange filter supplied by Imagenetics. The count determined the number of cells having two or more fluorescent signals per nucleus. Cells exhibiting trisomy 8 each have three fluorescent signals. A total of two slides for each of Examples 1-1 through 1-5 was counted.

Table 2 shows the average of two slides, percent diploid chromosome 8 and percent trisomy 8 determined for each of Examples 1-1 through 1-5, based on percent of total cells counted per slide:

TABLE 2

| EXAMPLE NUMBER | PERCENT CELLS WITH TWO SIGNALS | | PERCENT CELLS WITH THREE SIGNALS | |
|---|---|---|---|---|
| | Actual | Expected | Actual | Expected |
| 1-1 | 8.3 | — | 86.8 | — |
| 1-2 | 54.4 | 50.8 | 40.9 | 43.9 |
| 1-3 | 83.6 | 84.7 | 10.2 | 9.7 |
| 1-4 | 89.0 | 88.9 | 5.6 | 5.6 |
| 1-5 | 93.2 | — | 1.1 | — |

The actual values of 2 and 3 signals in the 100% K-562 and 100% GMO6912A were determined according to signal counts of the hybridization with the SpectrumCEP8 probe.

The hybridization count data showed that the expected count was achieved with less than 5% difference between the observed and expected percentages. The control compositions of the invention prepared by fixation of the cells only after mixing of the two cell sources, each of which comprised cells which were still capable of multiplication, resulted in reproducible artificial concentrations of aneuploid cells.

COMPARATIVE EXAMPLE 1

Comparative Example 1 describes Applicants' early attempts to prepare the compositions of the invention by mixing of two cell sources, each comprising fixed cells.

A fixed pellet of bone marrow exhibiting trisomy in various chromosomes was obtained from The Mayo Clinic, Rochester, Minn. The pellet was washed two times with Carnoy's fixative and stored in a refrigerator in 10 ml fixative. Supernatent containing cells was removed and the suspension was transferred to a new eppendorfer tube. The suspension was diluted by adding 0.1 ml additional Carnoy's fixative solution for each 0.1 ml of the cell suspension to produce a 1:10 dilution. The fixed cell suspension was diluted 1:1 with trypan blue to enable ease of counting with the hemocytometer. The cell counts were believed inaccurate because the suspension was evaporating too quickly resulting in cell motion and due to excessive clumping of the cells. Table 3 illustrates the variance in the cell counts obtained from counting the resulting suspension. It was expected that each quadrant would contain about the same number of cells in each chamber.

TABLE 3

| | CHAMBER 1 | CHAMBER 2 |
|---|---|---|
| QUADRANT 1 | 49 | 53 |
| QUADRANT 2 | 44 | 33 |
| QUADRANT 3 | 76 | 63 |
| QUADRANT 4 | 99 | 0 |

The average of counts in Chamber 1 was 67 cells compared to 49.6 in Chamber 2. Thus another method to obtain a better count of the fixed bone marrow trisomy sample was tried. Applicants then tried a 1:10 dilution of the fixed cells with phosphate buffered saline solution ("PBS"). The resulting suspensions were then attempted to be counted. The evaporation problem seemed to alleviate by dissolving the fixed cells in PBS. However, the cell clumping continued and accurate counts were again not obtained.

Because accurate cell counts are necessary for each of the two cell sources to permit mixing to achieve the desired amount of cells containing a specific abnormality. Applicants determined that it was simply not feasible to start with two fixed cell sources before mixing due to the cell clumping problem.

EXAMPLE 2

A separate set of control compositions using the K-562 and GMO6912A cell sources were made to examine reproducibility of the manufacture. The same procedure as used in Example 1 was followed.

A 1.0 ml of the K-562 cell suspension was diluted with 0.5 ml of trypan blue and cell count was determined on a hemocytometer to be $4.1 \times 10^5$ cells/cc. A 1.0 ml suspension of the GMO5912A cells was diluted with 0.5 ml of trypan blue and the cell count was determined to be $3.93 \times 10^5$ cells/cc. 9.0 ml of the K-562 suspension was then diluted slightly with 0.4 ml of RPMI to achieve an equivalent cell count to the GMO69 12A suspension.

The control compositions were then produced by mixing as follows:

Example 2-2:2 ml of K-562 suspension+1.5 ml GMO6912A suspension (about 50% trisomy 8)

Example 2-3:0.5 ml of K-562+4.32 ml GMO6912A (10% trisomy 8)

Example 2-4:0.25 ml K-562+5.25 GMO6912A (5% trisomy 8)

Example 2-1 was the control using 100% K-562 suspension. Example 2-5 was the control using 100% GMO6912A suspension.

All Examples were then harvested and suspended in Carnoy's fixative as in Example 1 and hybridization slides were produced as in Example 1. Two slides for each Example were made.

The slides were hybridized using the procedure of Example 1 with the same hybridization mix of Example 1 using SpectrumCEP 8 Orange Chromosome Enumeration Probe from Imagenetics.

The hybridization results were then counted, again using an observer blinded to the hybridization procedure. Table 4 shows the hybridization results.

TABLE 4

| EXAMPLE NUMBER | PERCENT CELLS WITH TWO SIGNALS | | PERCENT CELLS WITH THREE SIGNALS | |
|---|---|---|---|---|
| | Actual | Expected | Actual | Expected |
| 2-1 | 7.8 | — | 86.1 | — |
| 2-2 | 47.57 | — | 46.0 | 49.4 |
| 2-3 | 85.73 | — | 9.1 | 11.1 |
| 2-4 | 88.8 | — | 6.3 | 6.6 |
| 2-5 | 90.0 | — | 4.5 | — |

To check reproducibility of the hybridization results, a second set of two slides for each Example was then hybridized using the same procedure and hybridization mix and the hybridization results determined. Table 5 lists the results.

TABLE 5

| EXAMPLE NUMBER | PERCENT CELLS WITH TWO SIGNALS | | PERCENT CELLS WITH THREE SIGNALS | |
|---|---|---|---|---|
| | Actual | Expected | Actual | Expected |
| 2-1 | 8.13 | — | 84.35 | — |
| 2-2 | 47.92 | — | 44.9 | 49.4 |
| 2-3 | 83.36 | — | 9.52 | 11.1 |
| 2-4 | 87.40 | — | 6.2 | 6.6 |
| 2-5 | 93.4 | — | 2.9 | — |

Comparing the results in Tables 4 and 5 shows good reproducibility for hybridization of the control compositions. The inventive compositions are reproducibly useful as control compositions for DNA chromosome enumeration probes.

The above description should not be considering limiting for the scope of the invention as other variations are possible. Rather, its scope is set out in the following claims.

We claim:

1. A control composition to measure performance of a test for determining molecular cytogenetic abnormality in individual cells comprising:
   (i) a suspension media, and
   (ii) a fixed cell mixture comprising
   (a) cells which are from at least two cell sources and which have similar morphology in their cell size, cell shape and cell configuration, wherein (1) at least one cell source exhibits at least one molecular cytogenetic abnormality in at least one chromosome and (2) likelihood of visual distinction between the cell sources by an observer is reduced,
   (b) a minimum total cell concentration above about 10,000 cells per milliliter, and
   (c) an artificial concentration of abnormality-containing cells exhibiting at least one molecular cytogenetic abnormality in at least one chromosome.

2. The control composition of claim 1 wherein the fixed cell mixture comprises cells from each of two human tumor cell sources.

3. The control composition of claim 1 wherein the artificial concentration of abnormality-containing cells is about 5 to about 95 percent of total cells in the cell mixture.

4. The control composition of claim 1 wherein the abnormality-containing cells exhibit chromosome specific aneuploidy in at least one chromosome.

5. The control composition of claim 4 having an artificial concentration of abnormality-containing cells which exhibit trisomy 8.

6. The control composition of claim 1 wherein the molecular cytogenetic abnormality comprises at least one of a chromosomal sequence translocation, a chromosomal sequence deletion or a chromosomal sequence amplification.

7. The control composition of claim 4 wherein the aneuploid cells exhibit chromosome specific aneuploidy in a chromosome selected from the group consisting of chromosomes 1 through 22, X and Y.

8. A control composition to measure performance of a test for determining chromosomal copy number of individual cells comprising:
   (i) a suspension media, and
   (ii) a fixed cell mixture comprising
   (a) cells which are from at least two cell sources and which have similar morphology in their cell size, cell shape and cell configuration, wherein (1) at least one cell source exhibits chromosome specific aneuploidy in at least one chromosome and (2) likelihood of visual distinction between the cell sources by an observer is reduced,
   (b) a minimum total cell concentration above about 10,000 cells per milliliter, and
   (c) an artificial concentration of aneuploid cells exhibiting chromosome specific aneuploidy in at least one chromosome.

9. The control composition of claim 1 wherein the fixed cell mixture comprises cells from each of at least two human tumor cell sources.

10. The control composition of claim 1 having an artificial concentration of aneuploid cells which exhibit trisomy 8.

11. The control composition of claim 1 wherein the artificial concentration of aneuploid cells is about 5 to about 95 percent of total cells in the cell mixture.

12. The control composition of claim 1 wherein the aneuploid cells exhibit chromosome specific aneuploidy in two or more chromosomes.

13. The control composition of claim 8 wherein the aneuploid cells are derived from a human tumor cell line.

14. The control composition of claim 8 wherein each of the cell sources comprises human tumor cells.

15. The control composition of claim 14 wherein the aneuploid cells exhibit chromosome specific aneuploidy in a chromosome selected from the group consisting of chromosomes 1 through 22, X and Y.

16. A container containing a control composition useful to measure performance of a test for determining chromosomal copy number of individual cells in a tissue sample comprising:
   (i) a suspension media, and
   (ii) a fixed cell mixture comprising
   (a) cells which are from at least two sources and have similar morphology in their cell size, cell shape and cell configuration, wherein (1) at least one cell source exhibits at least one molecular cytogenetic abnormality in at least one chromosome and (2) likelihood of visual distinction between the cell sources by an observer is reduced,
   (b) a minimum total cell concentration above about 10,000 cells per milliliter, and
   (c) an artificial concentration of abnormality-containing cells exhibiting a molecular cytogenetic abnormality in at least one chromosome.

17. The container of claim 16 wherein the abnormality-containing cells are human cells exhibiting chromosome specific aneuploidy in a chromosome selected from the group consisting of chromosomes 1 through 22, X and Y.

18. The container of claim 16 in a kit comprising at least one DNA probe.

19. A method of manufacturing a control composition to measure performance of a test for determination of molecular cytogenetic abnormalities, comprising: a cell suspension having an artificial concentration of abnormality-containing cells exhibiting a specific molecular cytogenetic abnormality, which method comprises:
   (a) mixing a first cell source with at least a second cell source in an appropriate ratio to produce an intermediate cell suspension, wherein (i) each of the first and second cell sources comprise cells in a suspension media which does not inhibit cell growth and cell concentration of the first and second cell sources is approximately equal, (ii) one of the cell sources comprises a predetermined artificial concentration of cells exhibiting the specific molecular cytogenetic abnormality and (iii) the first and second cell sources comprise cells having similar morpholgy in their cell size, cell shape and cell configuration;
   (b) treating the intermediate cell suspension by addition of a cell fixative solution to produce a control composition comprising fixed cells in suspension in a suspension media which does not sustain cell multiplication; and
   (c) determining the percent of total cells in the control composition exhibiting the artificial concentration of cells exhibiting the specific abnormality for a selected chromosome.

20. The method of claim 19 wherein the specific molecular cytogenetic abnormality is chromosome specific aneuploidy in at least one chromosome.

21. The method of claim 19 which further comprises: (d) producing a hybridization slide from the control compositions.

22. The control composition produced by the method of claim 19 comprising a minimum total cell concentration above about 10,000 cells per milliliter, wherein the abnormality-containing cells comprise cells from a human tumor cell line.

23. The control composition of claim 22 wherein the cells in the control composition exhibit chromosome specific aneuploidy in a chromosome selected from the group consisting of chromosomes 1 through 22, X and Y.

24. The control composition of claim 22 having an artificial concentration of cells exhibiting chromosome specific aneuploidy in the range of 5 to 95 percent of total cells in the control composition.

25. A microscope examination slide comprising the control composition of claim 1.

26. A microscope examination slide comprising the control composition of claim 8.

27. A microscope examination slide comprising the control composition of claim 22.

* * * * *